United States Patent [19]

Schmitt et al.

[11] Patent Number: 5,472,991
[45] Date of Patent: Dec. 5, 1995

[54] TWO-STAGE PHOTOCURING PROCESS FOR A DENTAL COMPOSITION

[75] Inventors: Werner Schmitt, Starnberg; Peter Jochum, Seefeld; Klaus Ellrich, Wörthsee, all of Germany

[73] Assignee: 501 Espe Stiftung & Co. Produktions-Und, Seefeld, Germany

[21] Appl. No.: 278,142

[22] Filed: Jul. 21, 1994

Related U.S. Application Data

[62] Division of Ser. No. 946,553, Sep. 17, 1992, abandoned, which is a continuation of Ser. No. 701,345, May 9, 1991, abandoned, which is a continuation of Ser. No. 298,664, Jan. 18, 1989, abandoned.

[30] Foreign Application Priority Data

Jan. 20, 1988 [DE] Germany ............... 38 01 511.0

[51] Int. Cl.[6] ............... C08F 2/50; A61C 5/00; C08J 3/28; C08K 3/40
[52] U.S. Cl. ............... 522/4; 522/28; 522/908; 522/913; 523/116; 433/228.1; 433/215
[58] Field of Search ............... 522/4, 18, 28, 522/8, 12, 908, 913; 523/116; 433/228.1, 215

[56] References Cited

U.S. PATENT DOCUMENTS

| | | | |
|---|---|---|---|
| 4,089,763 | 5/1978 | Dart et al. | 522/908 |
| 4,131,729 | 12/1978 | Schmitt et al. | 522/908 |
| 4,304,893 | 12/1981 | Orlowski | 522/908 |
| 4,459,193 | 7/1984 | Ratcliffe et al. | 522/908 |
| 4,710,523 | 12/1987 | Lechtken et al. | 522/28 |
| 4,737,593 | 4/1988 | Ellrich et al. | 430/910 |
| 4,744,827 | 5/1988 | Winkel et al. | 522/28 |
| 4,771,084 | 9/1988 | Kubota et al. | 522/10 |

*Primary Examiner*—Susan W. Berman
*Attorney, Agent, or Firm*—Birch, Stewart, Kolasch & Birch

[57] ABSTRACT

The invention relates to photopolymerizable dental compositions of ethylenically unsaturated monomers and/or polymers thereof which are curable in two curing steps. Besides being comprised of fillers, said compositions also contain a photoinitiator component I having a light absorption maximum of <450 nm and a molar extinction of the light absorption of <10 at wavelengths of 470 nm or higher, and a photoinitiator component II having a molar extinction of the light absorption of >20 at least at one wavelength of at least >450 nm.

13 Claims, No Drawings

TWO-STAGE PHOTOCURING PROCESS FOR A DENTAL COMPOSITION[<]med

This application is a divisional of application Ser. No. 07/946,553, filed on Sep. 17, 1992, now abandoned, which is a Rule 62 Continuation application of Ser. No. 07/701,345, filed May 9, 1991, now abandoned, and which is a Rule 62 Continuation application of Ser. No. 07/298,664, filed Jan. 18, 1989, now abandoned, the entire contents of which are hereby incorporated by reference.

BACKGROUND OF THE INVENTION

1. Field of the Invention

The present invention relates to dental compositions, more particularly, the present invention relates to tooth filling compositions, that are curable in two curing steps.

2. Discussion of Related Art

Essentially all commercial dental compositions which meet the high cosmetic standards, especially tooth filling compositions, consist of synthetic resins which contain organic or inorganic fillers (the so-called composites). The proportions of these fillers may vary from 30 to 90% by weight. In particular, in the field of the so-called side tooth composites, it has been proved desirable to incorporate the maximum amount of hard inorganic fillers in tooth filling compositions in order to characterize the final restoration with sufficient hardness. In particular, the use of silanized, finely granular fillers, such as quartz or X-ray-opaque glass, have proved to be especially advantageous for preparing abrasion-resistant side tooth composites. Such tooth filling compositions favorably contain from 80 to 90% by weight of an inorganic filler material. The fillers normally employed have an average particle size of from 1 to 15 µm. Conventionally, substantially finer fillers within the range of from 0.02 to 0.05 µm are employed together with the above mentioned fillers in order to render the compositions sufficiently plastic.

It has been found to be particularly advantageous to employ the so-called hybrid composites in the side tooth composite area, because with the simultaneous use of from 5 to 25% by weight of filler particles having an average particle size of from 0.02 to 0.05 µm and from 65 to 85% by weight of filler particles having an average particle size of from 1 to 15 µm, especially abrasion resistant tooth filling compositions are obtained. In this connection it has been found that such side tooth composites possess sufficient hardness to resist wear inside the mouth for a sufficiently long period of time. On the other hand, the problem has arisen that after placing and curing the filling in the tooth, the curing normally effected with visible light, any existing excess can be distinguished from the surrounding tooth material only with difficulty. On one hand, this is due to the possible tooth-like coloring of the material, (in contrast to the classical amalgam filling), and on the other hand, this is also due to the tooth-like hardness of such hard tooth filling compositions.

A dentist encounters the same problems with laying tooth fillings, when cementing inlays, onlays, and facing shells made of sufficiently transparent material, e.g., porcelain or synthetic resin. At the present time, light-curing materials are preferably employed for these purposes, but which are subjected to partially to post-hardening, by a subsequent redox process. Since the initial fixing is invariably initiated with a photopolymerization, the problems, as in the placing of the tooth fillings, reside in the finishing off of these fillings, particularly in the finishing steps of removing the excess material and affecting occlusion by abrasion, these steps have become very difficult for the dentist, since these steps are very time consuming and cause a high wear of the polishing instruments. Accordingly, for this purpose, only very expensive diamond tipped instruments can be employed, and due to the use of such instruments, there is always an existing risk that, after the placement of the filling, the enamel rim, i.e., the marginal region of the existing tooth, is in danger of being damaged during polishing.

It is the object of the present invention to provide novel dental compositions, particularly tooth filling compositions, which are curable in two curing steps and which do not exhibit the drawbacks of the prior art. In particular, the new dental compositions are easily processable and when cured, are characterized with an excellent final hardness of the dental material.

SUMMARY OF THE INVENTION

The subject matter of the present invention relates to a dental composition comprising
(a) 5 to 70% by weight, based on the weight of (a) and (b), of an ethylenically unsaturated, polymerizable monomer, a polymer of said monomer or a mixture thereof,
(b) 30 to 95% by weight, based on the weight of (a) and (b), of fillers,
(c) 0.05 to 3% by weight, based on the weight of (a), of a photoinitiator component I having a light absorption maximum of <450 nm and a molar extinction of the light absorption of <10 at wave lengths of 470 nm or higher,
(d) 0.05 to 3% by weight, based on the weight of (a), of a photoinitiator component II having a molar extinction of the light absorption of >20 at least at one wavelength of >450 nm, and
(e) optionally pigments, x-ray-opaque additives, thixotropy adjuvants or mixtures thereof.

The present invention further relates to a process for curing said dental compositions comprising curing the compositions in a first curing step with light from the wavelength range of substantially >450 nm, preferably >470 nm and forming the surface of a partially-cured dental composition, said formed surface is irradiated in a second curing step with light which includes distinct ranges of wavelengths of <450 nm.

Yet further, the subject matter of the present invention relates to the use of a combination of the photoinitiator component I having a light absorption maximum of <450 nm and a molar extinction of the light absorption of <10 at wavelengths of 470 nm or higher, and of the photoinitiator component II having a molar extinction of the light absorption of >20 at least at one wavelength of >450 nm, for preparing dental compositions which are curable in two curing steps.

DETAILED DESCRIPTION OF THE INVENTION

The photoinitiator components I and II used according to the present invention, preferably are each contained in an amount of from 0.1 to 2% by weight, particularly from 0.5 to 1.5% by weight, based on the weight of (a).

The photoinitiator components I and II according to the present invention need not be used at equal concentrations. The optimum concentration of components I and II individually, depend on the light intensity of the lamp used for curing, and on the selected wavelength range for the activation of the photoinitiator component II. The final hardness in this context defines the surface hardness which is obtainable upon complete curing. The surface hardness can be measured, for example, according to DIN specification 53456.

Suitable photoinitiator components I are all of the known photoinitiators having a light absorption maximum of <450 nm and a molar extinction of the light absorption of <10 at wavelengths of 470 nm or higher. Photoinitiators having an absorption maximum of <430 nm, a molar extinction of <10 at wavelengths of 470 nm or higher, and a molar extinction at 400 nm of >25 are especially preferred. Monoacylphosphine oxides and monoacylphosphine sulfides have proved to be suitable initiators, e.g., 2,4,6-trimethyl benzoyldiphenyl phosphinoxide, as described in European patent publications 73413, 7508, 47902, and 57474. Especially suitable initiators are primarily bisacylphosphine oxides, such as those known from European patent publication 184095. These bisacylphosphine oxides have the general formula

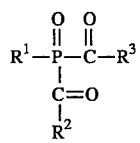

wherein $R^1$ is a straight-chain or branched $C_{1-18}$ alkyl radical, a cyclohexyl, cyclopentyl, phenyl, naphthyl, or biphenyl radical, a cyclopentyl, cyclohexyl, phenyl, naphthyl, or biphenyl radical which is substituted with F, Cl, Br, I, $C_1$-$C_{12}$-alkyl and/or $C_1$-$C_{12}$alkoxyl, or a S- or N-containing 5- or 6-membered heterocyclic ring, and $R^2$ and $R^3$, which are the same or different, each represent a cyclohexyl, cyclopentyl, phenyl, naphthyl, or biphenylyl radical, a cyclopentyl, cyclohexyl, phenyl, naphthyl, or biphenyl radical which is substituted with F, Cl, Br, I, $C_1$-$C_4$-alkyl and/or $C_1$-$C_4$-alkoxyl, or a S- or N-containing 5- or 6-membered heterocyclic = ring; or $R^2$ and $R^3$ are joined to form a ring which contains 4 to 10 carbon atoms and may be substituted by 1 to 6 $C_{1-4}$-alkyl radicals.

Among these, compounds which are particularly preferred, wherein $R^1$ of the general formula of the bisacylphosphine oxides represents decyl, phenyl, naphthyl, 4-biphenylyl, 2-methylphenyl, 1-methylnaphthyl, 2,5-dimethylphenyl, 4-propylphenyl, 4-octylphenyl, 4-chlorophenyl or 4-ethoxyphenyl, and $R^2$ and $R^3$, each represent phenyl, naphthyl, 2,6-dichloro- phenyl, 2,6-dimethoxyphenyl, 2-methylnaphthyl, 2-methoxy-naphthyl, 2,6-dimethylphenyl or 2,4,6-trimethylphenyl.

Preferably $R^2$ and $R^3$ have the same meanings. Examples of such compounds are bis(2,6-dichlorobenzoyl)-phenylphosphine oxide, bis(2,6-dichlorobenzoyl)- 2,5-dimethylphenylphosphine and bis(2,6-dichlorobenzoyl)- 4-n-propylphenylphosphine oxide.

These photoinitiators have absorption maximum at 360 to 410 nm, i.e., at >400 nm, and still have considerable molar extinctions (e.g. from 400 to 3000 at 400 nm). At 470 nm or higher, these compounds no longer exhibit measurable molar extinction.

All of the prior art photoinitiators having a molar extinction of light absorption of >20 at a wavelength of at least >450 nm, e.g., α-diketones, are suitable to be used as photoinitiator component II. The photoinitiator II preferably has a molar extinction of > 20 at a wavelength at least between >450 and 500, especially between 470 and 500 nm. Camphor quinone having an absorption maximum at about 470 nm is especially well suited. The photoinitiator component II is preferably so selected as to the type and quantity that it would lead to a fully cured material having a maximum of 70%, preferably a maximum of 50% of the hardness which the same material would have after having been cured exclusively with the photoinitiator component I. In this case the photoinitiator component II can also be used in combination with an activator, e.g. a tertiary amine, provided that the hardness of the material cured with the photoinitiator component II does not exceed 70% of the hardness of the same material cured exclusively with the photoinitiator component I.

Compositions are especially well suited for use as dental composites in which the photoinitiator component II is so selected as to the type and quantity that upon curing with light of a wavelength of substantially >450 nm, preferably substantially >470 nm, a surface hardness of <200 MPa, preferably <150 MPa, and most preferably <100 MPa, is obtained.

An especially suitable combination of photoinitiators consists of a mixture of 0.05 to 3% by weight of bisacylphosphine oxide and 0.05 to 3% by weight of camphor quinone, based on the weight of (a).

It has been found that dental compositions according to the present invention can be cured in two curing steps. In a first curing step only the photoinitiator component II is activated by the selection of the light source or by filtering out the wavelength range of <450 nm. The light of longer wavelength and lesser energy produces relatively few reactive radicals which, in the absence of activators, such as amines, result in only a partial curing of the ethylenically unsaturated polymerizable monomers employed. According to the present invention, the hardness of the material fully cured with the photoinitiator component II is at a maximum of 70%, preferably 50% of the final hardness which is obtained with the sole use of the photoinitiator component I employed, and with the use of a light of lower wavelength (<450 nm).

In a second step the final hardness of the material is reached by the use of a source of light with distinct ranges of light of <450 nm wavelength. This can be accomplished, for example, by omitting the optical cut-off filter employed in the first curing step, and by a repeated exposure.

The separation of the wavelength ranges for the two curing steps can be effected suitably with cut-off filters in the range of 450 to 480 nm. The selection of the cut-off filter, however, is dependent on the photoinitiator component II employed. The use of camphor quinone cut-off filters in the range of 465 to 480 nm have proved effective, especially in the range of 470 to 480 nm.

The advantage provided to a user of such dental compositions resides in that the dentist, for example, who has to fill a cavity can fix the material in a first curing step by using a light source with light portions of substantially >470 nm, and can cure the material up to a maximum of 70%, preferably 50%, of the final hardness. Particularly with side tooth composites the dentist can obtain a hardness which would allow the material to still be capable of being worked with carving tools. Also, subsequent polishing and refining can be accomplished with distinctly less loss of the material (at the instrument). After termination of these operations the user can bring the dental compositions to a final hardness by curing with a light of <450 nm (or substantial ranges of light in this range), and thus, a fully cured filling which can offer sufficient resistance to the abrasive forces occurring in the mouth has been made.

A further advantageous field of use of the compositions of the present invention is as photo-curing cement materials can be made by the following means. After the first curing step, sufficiently transparent inlays and facing shells can be mounted on a tooth fastened by the composition with a further partial-curing of the composition and thereafter the rim of the preparation can be worked with carving instruments with distinctly lesser wear on the instrument and on the tooth. After the work has been completed, it is subjected to the second exposure step to obtain the final hardness of the cementing material.

In an advantageous embodiment both photoinitiator components I and II have a sufficient absorption range in the range from 400 to 500 nm so that they can both be activated with the same commercial dental irradiation unit. The separation of the two curing steps can then be effected by a simple mounting and removal of the cut-off filters.

Ethylenically unsaturated polymerizable monomers and polymers suited for dental purposes include, for example, monomeric and polymeric acrylates and methacrylates. Frequently used polymerizable dental compositions are the long-chain monomers of U.S. Pat. No. 3,066,112 which are based on bisphenol-A and glycidyl methacrylate or derivatives thereof formed by the addition of isocyanates. Also included are acrylic acid and methacrylic acid esters of monohydric or polyhydric alcohols, e.g. methyl and ethyl methacrylate, especially the esters of polyhydric alcohols such as triethylene glycol di(meth)acrylate, ethylene glycol di(meth)acrylate, hexanediol di(meth)acrylate and trimethylolpropane tri(meth)acrylate. Further included are compounds of the bisphenol A type—diethyl(meth)acrylate and bisphenol A—dipropyl(meth)acrylate, which are described in German Patent Specification 28 16 823. Especially suitable compounds are the diacrylates and dimethacrylates of bis-hydroxymethyl-tricyclo-[$5.2.1.0.^{2,6}$]decane. Also employable are the reaction products of diisocyanates and hydroxyalkyl(meth)acrylates, which are described in German laid-open specification 2312559.

Of course, the mixtures of monomers and/or of unsaturated polymers prepared therefrom can be used.

Conventional components of dental compositions, in addition to the saturated and unsaturated polymers, include pigments, dyes, and inorganic fillers. Inorganic fillers may be quartz, ground glasses, silica gels, and silicic acids, also in granular form. The inorganic fillers may be contained in a concentration of from 30 to 95% by weight, based on the weight of (a) and (b). A preferred concentration range of inorganic filler material is 60 to 95% by weight; a range of 75 to 90% by weight, based on the weight of (a) and (b), is especially preferred.

In a preferred embodiment the filler proportion consists, on the one hand, of 1 to 25% by weight, preferably 5 to 20% by weight, of micro-fine fillers, such as pyrogenic silica types having an average particle size of 0.02 to 0.05 μm, and 65 to 89% by weight of finely divided inorganic filler having an average particle size from 1 to 15 μm, preferably 2 to 10 μm, particularly preferred from 3 to 8 μm. The filler concentration is based on the weight of (a) and (b).

For easier incorporation into the polymer matrix it may be advantageous to render the fillers and optionally the X-ray-opaque additives hydrophobic. Conventional agents for imparting water repellency are silanes, e.g., trimethoxymethacryloxypropyl silane.

In a preferred embodiment, all of the inorganic fillers employed are treated with silane, preferably with trimethoxymethacryloxypropyl silane. The amount of silane employed normally ranges from 0.5 to 10% by weight, based on inorganic filler, preferably from 1 to 6%, and particularly preferred from 2 to 5% by weight, based on the weight of the inorganic filler.

As the X-ray-opaque additives, the heavy metal fluorides mentioned in European patent publication 238025 can be employed.

In a preferred embodiment of the present invention, 5 to 30% by weight of the X-ray-opaque additives, especially yttrium fluoride, based on the weight of (a)+(b), are employed. An amount from 10 to 25% by weight of yttrium fluoride is particularly preferred.

EXAMPLE 1

Photopolymerizable Tooth Filling Composition

70 Parts by weight of bis-acryloxymethyl-tricyclo-[$5.2.1.0.^{2,6}$]decane and 30 parts by weight of 2,2-bis- 4-(3-methacryloxy-2-hydroxypropoxy)-phenylpropane (bis-GMA) are stirred while being heated until a clear solution is obtained. The solution is cooled to room temperature and the weight percentages of the photoinitiators and optionally an activator listed in Table 1 are added to form a mixture. The mixture is stirred until a clear solution (1) is obtained.

20 g of this solution (1) are mixed with 2 g of silanized pyrogenic silica (Aerosil 0×50, a product of Degussa) and 100 g of silanized quartz pigmented to resemble the color of teeth (average particle size about 6 μm), and kneaded to obtain a tooth filling composition of uniform pasty consistency. Table 1 shows the physical data of pastes obtained with this formulation.

TABLE 1

| Paste | Photoinitiators/ Activators (% by Wt., based on Monomer Mixture) | Surface Hardness according to DIN 53456 [MPa] | | Resistance to Pressure [MPa] |
|---|---|---|---|---|
| | | 1st Activation*) | 2nd Activation**) | |
| 1 (commercial composition) | 0.2 camphor quinone 1 dimethyl-ethanolamine | 460 | 475 | 350 |
| 2 (invention) | 0.2 camphor quinone 0.5 bis-(2,6-di-chlorobenzoyl)- | 123 | 478 | 370 |

TABLE 1-continued

| Paste | Photoinitiators/ Activators (% by Wt., based on Monomer Mixture) | Surface Hardness according to DIN 53456 [MPa] | | Resistance to Pressure [MPa] |
|---|---|---|---|---|
| | | 1st Activation[x] | 2nd Activation[xx] | |
| | 4-n-propyl-phenylphosphine oxide | | | |

[x]) exposure for 10 sec. with ELIPAR(R) apparatus (Messrs. ESPE), through cut-off filter 475 nm (diameter 8 mm, thickness 2 mm, Messrs. Schott)
[xx]) exposure for 20 sec. with ELIPAR(R) apparatus (Messrs. ESPE), but without cut-off filter

RESULT

The paste (2) according to the present invention can be incipiently hardened in a first activating step, but after the 1st activation the attained hardness is only about 24% of the attainable final hardness. After this activating step the material can no longer be plastically shaped, but it can still be contoured with a sharp-edged instrument, such as an amalgam carver. Fine fissures and a perfect rim can be formed. The occlusion does not require to be effected by abrasion with expensive diamond tools, but can be accomplished with less expensive hard metal cutters. After the optimum surface formation is obtained, the final hardness is attained in a 2nd activation step.

After the 1st activation of paste (1) (comparison), the hardness of the surface attained, is almost to the degree of the hardness attained after the second activation.

EXAMPLE 2

X-Ray-Opaque Photopolymerizable Tooth Filling Compositions 9 g of solution (1) are mixed with 6 g of silanized pyrogenic silica, 16.5 g of finely divided yttrium fluoride (average particle size about 1 μm) and 60 g silanized quartz pigmented to resemble the color of teeth (average particle size about 6 μm) and kneaded to form a tooth filling composition having a uniformly pasty consistency. The physical data of the two pastes with different initiator components are compiled in Table 2.

RESULT

The paste (4) according to the present invention can be incipiently cured in a first activating step, but after the 1st activation the attained hardness is only about 14% of the attainable final hardness. After this activating step the material can no longer be plastically shaped, but it can still be contoured with sharp-edge instruments such as amalgam carvers. Fine fissures and a perfect rim can be formed. The occlusion does not require to be effected by abrasion with expensive diamond finishing tools; but can be accomplished with less expensive hard metal cutters. After the optimum surface formation is obtained the final hardness is attained in a 2nd activating step.

After the 1st activation of paste (3) (comparison), the hardness of the surface attained is almost to the degree of the hardness attained after the second activation.

EXAMPLE 3

50 Parts by weight of bis-acryloxymethyl tricyclo-[$5.2.1.0.^{2,6}$]-decane and 50 parts by weight of the reaction product of 2 mols of acrylic acid and 1 mol of the bis-ethoxylated bis-hydroxy-methyl-tricyclo-[ $5.2.1.0.^{2,6}$]-decane are stirred while being heated until a clear solution is obtained. The solution is cooled to room temperature and 0.6% by weight of camphor quinone and 1% by weight of bis-(2,6-dichlorobenzoyl)- 4-n-propylphenylphosphine oxide are added to form a mixture. The mixture is stirred until a clear solution (2) is obtained.

TABLE 2

| Paste | Photoinitiators/ Activators (% by wt., based on Monomer Mixture) | Surface Hardness according to DIN 53456 [MPa] | | Resistance to Pressure [MPa] |
|---|---|---|---|---|
| | | 1st Activation[x] | 2nd Activation[xx] | |
| 3 (comparison) | 0.2 camphor quinone dimethyl ethanolamine | 600 | 630 | 400 |
| 4 (invention) | 0.2 camphor quinone 0.5 bis-(2,6-dichlorobenzoyl)- 4-n-propyl-phenylphosphine oxide | 85 | 630 | 420 |

[x]) exposure for 10 sec. with ELIPAR(R) apparatus (Messrs. ESPE), through cut-off filter 475 nm (diameter 8 mm, thickness 2 mm, Messrs. Schott)
[xx]) exposure for 20 sec. with ELIPAR(R) apparatus (Messrs. ESPE), but without cut-off filter 56 g of solution (2), are mixed with 15 g of calcium fluoride, 9.2 g of silanized pyrogenic silica, 30.3 g of yttrium fluoride, and 6 g of pigment, and kneaded to obtain a cementing composition of uniform pasty but flowable consistency. After exposure of the cementing composition for 20 seconds in the ELIPAR® apparatus (Messrs. ESPE) through a cut-off filter 475 nm (8 mm diameter, 2 mm thickness, Messrs. Schott) the resultant cementing material has a surface hardness, measured according to DIN 53 456, of 65 MPa, and an incipiently hardened layer thickness of 2.5 mm. In this condition said material is capable of being readily carved so that the excess cement can be easily removed. The film thickness of the cementing material is 10 μm. After exposure in the Elipar® apparatus (Messrs. ESPE) for 20 seconds, but without the use of a cut-off filter, the final hardness of the cementing material is 100 MPa.

What is claimed:

1. A process for curing a photocurable dental composition comprising:
   first irradiating said dental composition comprising:
   (a) 5 to 70% by weight based on the weight of and (b), of an ethylenically unsaturated polymerizable monomer, an unsaturated polymer of said monomer or a mixture thereof, wherein said ethylenically unsaturated polymerizable monomer is an acrylate or a methacrylate,
   (b) 30 to 95% by weight, based on the weight of (a) and (b), of fillers,
   (c) 0.05 to 3% by weight, based on the weight of (a), of a photoinitiator (I) having a light absorption maximum of <450 nm and a molar extinction coefficient of <10 at wavelengths of 470 nm or higher,
   (d) 0.05 to 3% by weight, based on the weight of (a), of a photoinitiator (II) having a molar extinction coefficient of >20 at a wavelength of >450 nm, and
   (e) optionally pigments, X-ray-opaque additives, thixotropy adjuvants or mixtures thereof;
   with light of wavelengths >450 nm to effect partial curing of said dental composition to between 50 and 70% of its maximum hardness; and
   subsequently irradiating said dental composition with light including wavelengths <450 nm to effect complete curing of said dental composition.

2. The process according to claim 1, further comprising the step of removing excess amounts of said dental composition after said first irradiation step, but before said subsequent irradiation step.

3. The process according to claim 1, wherein said photoinitiator (II) and any activators therefor, are selected such that the surface hardness of said dental composition after partial curing is <200 MPa.

4. The process according to claim 3, wherein said photoinitiator (II) is an α-diketone.

5. The process according to claim 4, wherein said photoinitiator is camphor quinone.

6. The process according to claim 1, wherein said photoinitiator (I) has an absorption maximum from 360 to 410 nm.

7. The process according to claim 6, wherein said photoinitiator (I) has a molar extinction coefficient >25 at 400 nm.

8. The process according to claim 7, wherein said photoinitiator (I) is a bisacylphosphine oxide.

9. The process according to claim 8, wherein said bisacylphosphine oxide is represented by the formula:

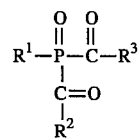

wherein
$R^1$ is a straight-chain or branched $C_{1-18}$-alkyl radical, a cyclohexyl, cyclopentyl, phenyl, naphthyl or biphenylyl radical; a cyclohexyl, cyclopentyl, phenyl, naphthyl or biphenylyl radical substituted with F, Cl, Br, I, $C_1$–$C_{12}$-alkyl, $C_1$–$C_{12}$-alkoxyl, or mixtures thereof; a S or N containing 5-membered or 6-membered heterocyclic ring, and $R^2$ and $R^3$, which may be identical or different, each represents a cyclohexyl, cyclopentyl, phenyl, naphthyl, or biphenylyl radical; a cyclopentyl, cyclohexyl, phenyl, naphthyl, or biphenylyl radical substituted with F, Cl, Br, I, $C_1$–$C_4$-alkyl, $C_1$–$C_4$-alkoxyl, or mixtures thereof; a S or N containing 5-membered or 6-membered heterocyclic ring; or $R^2$ and $R^3$ are joined to form a ring containing from 4 to 10 carbon atoms and optionally substituted by 1 to 6 $C_{1-4}$-alkyl radicals.

10. The process according to claim 1, wherein the wavelengths of said first irradiation step are obtained by filtering out light with wavelengths <450 nm with a suitable optical cut-off filter and the wavelengths of said subsequent irradiation step are obtained by omitting said optical cutoff filter.

11. A process of preparing a dental tooth filling, said method comprising the steps of:
   Step 1) providing a two-stage curable dental composition comprising:
   (a) 5 to 70% by weight based on the weight of (a) and (b), of an ethylenically unsaturated polymerizable monomer, an unsaturated polymer of said monomer or a mixture thereof, wherein said ethylenically unsaturated polymerizable monomer is an acrylate or a methacrylate,
   (b) 30 to 95% by weight, based on the weight of (a) and (b), of fillers,
   (c) 0.05 to 3% by weight, based on the weight of (a), of a photoinitiator (I) having a light absorption maximum of <450 nm and a molar extinction coefficient of <10 at wavelengths of 470 nm or higher,
   (d) 0.05 to 3% by weight, based on the weight of (a), of a photoinitiator (II) having a molar extinction coefficient of >20 at a wavelength of >450 nm, and
   (e) optionally pigments, X-ray-opaque additives, thixotropy adjuvants or mixtures thereof;
   Step 2) shaping the dental composition to the desired shape;
   Step 3) irradiating said dental composition with light of wavelengths >450 nm, thus obtaining a partially-cured dental composition, with up to 70% of its maximum hardness;
   Step 4) removing any excess amount of said dental composition with carving tools;
   Step 5) irradiating said remaining dental compositions with light including wavelengths <450 nm, to obtain a fully-cured, dental tooth filling at its final hardness.

12. The method of claim 11, wherein in the two-stage curable dental composition:
   the photoinitiator (I) comprises a bisacylphosphine oxide of the general formula:

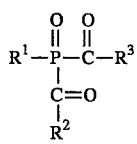

wherein
- $R^1$ is a straight-chain or branched $C_{1-18}$-alkyl radical, a cyclohexyl, cyclopentyl, phenyl, naphthyl or biphenylyl radical; a cyclohexyl, cyclopentyl, phenyl, naphthyl or biphenylyl radical substituted with F, Cl, Br, I, $C_1$–$C_{12}$-alkyl, $C_1$–$C_{12}$-alkoxyl, or mixtures thereof; a S or N containing 5-membered or 6-membered heterocyclic ring, and
- $R^2$ and $R^3$, which may be identical or different, each represents a cyclohexyl, cyclopentyl, phenyl, naphthyl, or biphenylyl radical; a cyclopentyl, cyclohexyl, phenyl, naphthyl, or biphenylyl radical substituted with F, Cl, Br, I, $C_1$–$C_4$-alkyl, $C_1$–$C_4$-alkoxyl, or mixtures thereof; a S or N containing 5-membered or 6-membered heterocyclic ring; or
- $R^2$ and $R^3$ are joined to form a ring containing from 4 to 10 carbon atoms and optionally substituted by 1 to 6 $C_{1-4}$-alkyl radicals.

13. A process for mounting sufficiently transparent dental inlays, onlays and facing shells, comprising the following steps:

Step 1) fastening said inlay, onlay or facing shell to a tooth with a composition comprising;
  (a) 5 to 70% by weight based on the weight of (a) and (b), of an ethylenically unsaturated polymerizable monomer, a polymer of said monomer or a mixture thereof, wherein said ethylenically unsaturated polymerizable monomer is an acrylate or a methacrylate,
  (b) 30 to 95% by weight, based on the weight of (a) and (b), of fillers,
  (c) 0.05 to 3% by weight, based on the weight of (a), of a photoinitiator (I) having a light absorption maximum of <450 nm and a molar extinction coefficient of <10 at wavelengths of 470 nm or higher,
  (d) 0.05 to 3% by weight, based on the weight of (a), of a photoinitiator (II) having a molar extinction coefficient of >20 at a wavelength of >450 nm, and
  (e) optionally pigments, X-ray-opaque additives, thixotropy adjuvants or mixtures thereof;

Step 2) irradiating the composition in a first curing step with light of wavelengths >450 nm, forming a resultant mounted product;

Step 3) carving any excess composition from the rim of the mounted product with carving instruments, to form a finished product; and Step 4) irradiating the finished product in a final curing step with light including wavelengths <450 nm, securing the finished product to the tooth.

* * * * *